(12) United States Patent
Michelson

(10) Patent No.: US 7,534,254 B1
(45) Date of Patent: May 19, 2009

(54) THREADED FRUSTO-CONICAL INTERBODY SPINAL FUSION IMPLANTS

(75) Inventor: Gary Karlin Michelson, Venice, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 08/480,908

(22) Filed: Jun. 7, 1995

Related U.S. Application Data

(60) Continuation-in-part of application No. 08/396,414, filed on Feb. 27, 1995, now Pat. No. 6,080,155, and a continuation-in-part of application No. 08/390,131, filed on Feb. 17, 1995, now Pat. No. 5,593,409, application No. 08/396,414, which is a continuation-in-part of application No. 08/074,781, filed on Jun. 10, 1993, now Pat. No. 5,484,437, which is a continuation-in-part of application No. 07/968,240, filed on Oct. 29, 1992, which is a continuation of application No. 07/698,674, filed on May 10, 1991, now abandoned, which is a division of application No. 07/205,935, filed on Jun. 13, 1988, now Pat. No. 5,015,247.

(51) Int. Cl.
*A61B 17/70* (2006.01)
(52) U.S. Cl. .................. 606/246; 623/17.11
(58) Field of Classification Search ............ 606/60–61, 606/72–79, 246; 623/16, 17, 16.11, 17.11
See application file for complete search history.

(56) References Cited

U.S. PATENT DOCUMENTS

| 350,420 | A | 10/1886 | Dillon |
| 1,137,858 | A | 4/1915 | Craig |
| 2,065,659 | A | 12/1936 | Cullen |
| 2,181,746 | A | 11/1939 | Siebrandt |
| 2,243,718 | A | 5/1941 | Moreira |
| 2,372,622 | A | 3/1945 | Fassio |
| 2,514,665 | A | 7/1950 | Myller |

(Continued)

FOREIGN PATENT DOCUMENTS

DE 1961531 7/1970

(Continued)

OTHER PUBLICATIONS

Cloward, Ralph B.; Surgical Techniques for Lumbar Disc Lesions; Codman; Signature Serial 3.

(Continued)

*Primary Examiner*—Michael A. Brown
(74) *Attorney, Agent, or Firm*—Martin & Ferraro, LLP

(57) ABSTRACT

The present invention is directed to a variety of interbody spinal fusion implants having at least a partially frusto-conical configuration. An external thread is employed to increase implant stability and implant surface area, and for the purpose of advancing the spinal fusion implant into the fusion site. The spinal fusion implants of the present invention may be relatively solid or hollow and may have surface roughenings to promote bone ingrowth and stability. The spinal fusion implants of the present invention may have wells extending into the material of the implant from the surface for the purpose of holding fusion promoting materials and to provide for areas of bone ingrowth fixation.

183 Claims, 4 Drawing Sheets

U.S. PATENT DOCUMENTS

| | | |
|---|---|---|
| 2,537,070 A | 1/1951 | Longfellow |
| 2,543,780 A | 3/1951 | Hipps et al. |
| 2,677,369 A | 5/1954 | Knowles |
| 2,774,350 A | 12/1956 | Cleveland |
| 2,789,558 A | 4/1957 | Rush |
| 2,832,343 A | 4/1958 | Mose |
| 2,842,131 A | 7/1958 | Smith |
| 2,878,809 A | 3/1959 | Treace |
| 3,128,768 A | 4/1964 | Geistauts |
| 3,298,372 A | 1/1967 | Feinberg |
| 3,426,364 A | 2/1969 | Lumb |
| 3,486,505 A | 12/1969 | Morrison |
| 3,604,487 A | 9/1971 | Gilbert |
| 3,605,123 A | 9/1971 | Hahn |
| 3,618,611 A | 11/1971 | Urban |
| 3,709,219 A | 1/1973 | Halloran |
| 3,719,186 A | 3/1973 | Merig, Jr. |
| 3,720,595 A | 3/1973 | Hahn |
| 3,750,652 A | 8/1973 | Sherwin |
| 3,848,601 A | 11/1974 | Ma et al. |
| 3,855,638 A | 12/1974 | Pilliar |
| 3,866,510 A | 2/1975 | Elbes et al. |
| 3,867,728 A | 2/1975 | Stubstad et al. |
| 3,867,950 A | 2/1975 | Fischell |
| 3,875,595 A | 4/1975 | Froning |
| 3,888,260 A | 6/1975 | Fischell |
| 3,892,232 A | 7/1975 | Neufeld |
| 3,905,047 A | 9/1975 | Long |
| 3,915,151 A | 10/1975 | Kraus |
| 3,916,907 A | 11/1975 | Peterson |
| 3,918,440 A | 11/1975 | Kraus |
| 3,942,535 A | 3/1976 | Schulman |
| 3,948,262 A | 4/1976 | Zaffaroni |
| 3,952,334 A | 4/1976 | Bokros et al. |
| 3,987,499 A | 10/1976 | Scharbach et al. |
| 4,003,287 A | 1/1977 | Ziaylek, Jr. |
| 4,016,651 A | 4/1977 | Kawahara et al. |
| 4,027,392 A | 6/1977 | Sawyer et al. |
| D245,259 S | 8/1977 | Shen |
| 4,051,905 A | 10/1977 | Kleine |
| 4,059,115 A | 11/1977 | Jumashev et al. |
| 4,070,514 A | 1/1978 | Entherly et al. |
| 4,082,097 A | 4/1978 | Mann et al. |
| 4,086,701 A | 5/1978 | Kawahara et al. |
| 4,124,026 A | 11/1978 | Berner et al. |
| 4,142,517 A | 3/1979 | Stavropoulos et al. |
| 4,168,326 A | 9/1979 | Broemer et al. |
| 4,175,555 A | 11/1979 | Herbert |
| 4,177,524 A | 12/1979 | Grell et al. |
| 4,181,457 A | 1/1980 | Holmes |
| 4,197,850 A | 4/1980 | Schulman et al. |
| 4,206,516 A | 6/1980 | Pilliar |
| 4,222,128 A | 9/1980 | Tomonaga et al. |
| D257,511 S | 11/1980 | Zahn |
| 4,232,679 A | 11/1980 | Schulman |
| 4,237,948 A | 12/1980 | Jones et al. |
| 4,258,716 A | 3/1981 | Sutherland |
| 4,259,072 A | 3/1981 | Hirabayashi et al. |
| 4,262,369 A | 4/1981 | Roux |
| 4,271,832 A | 6/1981 | Evans et al. |
| D260,525 S | 9/1981 | Lassiter |
| 4,289,123 A | 9/1981 | Dunn |
| 4,293,962 A | 10/1981 | Fuson |
| 4,309,777 A | 1/1982 | Patil |
| 4,328,593 A | 5/1982 | Sutter et al. |
| 4,333,469 A | 6/1982 | Jeffcoat et al. |
| 4,341,206 A | 7/1982 | Perrett et al. |
| 4,349,921 A | 9/1982 | Kuntz |
| 4,356,572 A | 11/1982 | Guillemin et al. |
| 4,401,112 A | 8/1983 | Rezaian |
| 4,405,319 A | 9/1983 | Cosentino |
| 4,414,979 A | 11/1983 | Hirshorn et al. |
| 4,423,721 A | 1/1984 | Otte et al. |
| 4,439,152 A | 3/1984 | Small |
| 4,450,834 A | 5/1984 | Fischer |
| 4,484,570 A | 11/1984 | Sutter et al. |
| 4,492,226 A | 1/1985 | Belykh et al. |
| 4,497,320 A | 2/1985 | Nicholson et al. |
| 4,501,269 A | 2/1985 | Bagby |
| 4,507,115 A | 3/1985 | Kambara et al. |
| RE31,865 E | 4/1985 | Roux |
| 4,530,360 A | 7/1985 | Duarte |
| 4,535,374 A | 8/1985 | Anderson et al. |
| 4,535,485 A | 8/1985 | Ashman et al. |
| 4,542,539 A | 9/1985 | Rowe, Jr. et al. |
| 4,545,374 A | 10/1985 | Jacobson |
| 4,547,390 A | 10/1985 | Ashman et al. |
| 4,549,547 A | 10/1985 | Brighton et al. |
| 4,552,200 A | 11/1985 | Sinha et al. |
| 4,553,273 A | 11/1985 | Wu |
| 4,554,914 A | 11/1985 | Kapp et al. |
| D281,814 S | 12/1985 | Pratt et al. |
| 4,570,623 A | 2/1986 | Ellison et al. |
| 4,570,624 A | 2/1986 | Wu |
| 4,592,346 A | 6/1986 | Jurgutis |
| 4,599,086 A | 7/1986 | Doty |
| 4,600,000 A | 7/1986 | Edwards |
| 4,602,638 A | 7/1986 | Adams |
| 4,604,995 A | 8/1986 | Stephens |
| 4,608,052 A | 8/1986 | Van Kampen et al. |
| 4,611,581 A | 9/1986 | Steffee |
| 4,619,264 A | 10/1986 | Singh |
| 4,628,921 A | 12/1986 | Rousso |
| 4,634,720 A | 1/1987 | Dorman et al. |
| 4,636,217 A | 1/1987 | Ogilvie et al. |
| 4,636,526 A | 1/1987 | Dorman et al. |
| 4,645,503 A | 2/1987 | Lin et al. |
| 4,653,486 A | 3/1987 | Coker |
| 4,655,777 A | 4/1987 | Dunn |
| 4,661,536 A | 4/1987 | Dorman et al. |
| 4,664,567 A | 5/1987 | Edwards |
| 4,665,920 A | 5/1987 | Campbell |
| 4,677,883 A | 7/1987 | Lee |
| 4,677,972 A | 7/1987 | Tornier |
| 4,693,721 A | 9/1987 | Ducheyne |
| 4,696,290 A | 9/1987 | Steffee |
| 4,698,375 A | 10/1987 | Dorman et al. |
| 4,710,075 A | 12/1987 | Davison |
| 4,713,004 A | 12/1987 | Linkow et al. |
| 4,714,469 A | 12/1987 | Kenna |
| 4,721,103 A | 1/1988 | Freedland |
| 4,736,738 A | 4/1988 | Lipovsek et al. |
| 4,743,256 A | 5/1988 | Brantigan |
| 4,743,260 A | 5/1988 | Burton |
| 4,759,766 A | 7/1988 | Buettner-Janz et al. |
| 4,759,769 A | 7/1988 | Hedman et al. |
| 4,769,881 A | 9/1988 | Pedigo et al. |
| 4,781,591 A | 11/1988 | Allen |
| 4,790,303 A | 12/1988 | Steffee |
| 4,805,602 A | 2/1989 | Puno et al. |
| 4,820,305 A | 4/1989 | Harms et al. |
| 4,830,000 A | 5/1989 | Shutt |
| 4,834,757 A | 5/1989 | Brantigan |
| 4,848,327 A | 7/1989 | Perdue |
| 4,851,008 A | 7/1989 | Johnson |
| 4,863,476 A | 9/1989 | Shepperd |
| 4,863,477 A | 9/1989 | Monson |
| 4,865,603 A | 9/1989 | Noiles |
| 4,877,020 A | 10/1989 | Vich |
| 4,878,915 A | 11/1989 | Brantigan |
| 4,903,882 A | 2/1990 | Long |
| 4,904,260 A * | 2/1990 | Ray et al. ............... 623/17.12 |
| 4,904,261 A | 2/1990 | Dove et al. |
| 4,911,718 A | 3/1990 | Lee et al. |

| | | | |
|---|---|---|---|
| 4,913,144 A | 4/1990 | Del Medico | |
| 4,936,848 A | 6/1990 | Bagby | |
| 4,943,291 A | 7/1990 | Tanguy | |
| 4,955,885 A | 9/1990 | Meyers | |
| 4,955,908 A | 9/1990 | Frey et al. | |
| 4,957,495 A | 9/1990 | Kluger | |
| 4,960,420 A | 10/1990 | Goble et al. | |
| 4,961,740 A | 10/1990 | Ray et al. | |
| 4,968,316 A | 11/1990 | Hergenroeder | |
| 4,969,888 A | 11/1990 | Scholten et al. | |
| 4,987,904 A | 1/1991 | Wilson | |
| 5,015,247 A | 5/1991 | Michelson | |
| 5,015,255 A | 5/1991 | Kuslich | |
| 5,026,373 A | 6/1991 | Ray et al. | |
| 5,030,236 A | 7/1991 | Dean | |
| 5,055,104 A | 10/1991 | Ray | |
| 5,059,193 A | 10/1991 | Kuslich | |
| 5,062,845 A | 11/1991 | Kuslich et al. | |
| 5,071,437 A | 12/1991 | Steffee | |
| 5,084,050 A | 1/1992 | Draenert | |
| 5,102,414 A | 4/1992 | Kirsch | |
| 5,108,422 A | 4/1992 | Green et al. | |
| 5,112,336 A | 5/1992 | Krevolin et al. | |
| 5,116,304 A | 5/1992 | Cadwell | |
| 5,122,130 A | 6/1992 | Keller | |
| 5,123,926 A | 6/1992 | Pisharodi | |
| 5,133,755 A * | 7/1992 | Brekke | 623/23.51 |
| 5,171,278 A | 12/1992 | Pisharodi | |
| 5,192,327 A | 3/1993 | Brantigan | |
| 5,246,458 A | 9/1993 | Graham | |
| 5,258,031 A | 11/1993 | Salib et al. | |
| 5,263,953 A | 11/1993 | Bagby | |
| 5,279,292 A | 1/1994 | Baumann et al. | |
| 5,282,861 A | 2/1994 | Kaplan | |
| 5,292,252 A | 3/1994 | Nickerson et al. | |
| 5,306,309 A | 4/1994 | Wagner et al. | |
| 5,314,427 A | 5/1994 | Goble et al. | |
| 5,324,295 A | 6/1994 | Shapiro | |
| 5,352,229 A | 10/1994 | Goble et al. | |
| 5,360,430 A | 11/1994 | Lin | |
| 5,364,399 A | 11/1994 | Lowery et al. | |
| 5,370,662 A | 12/1994 | Stone et al. | |
| 5,370,697 A | 12/1994 | Baumgartner | |
| 5,393,036 A | 2/1995 | Sheridan | |
| RE34,871 E | 3/1995 | McGuire et al. | |
| 5,396,880 A | 3/1995 | Kagan et al. | |
| 5,397,359 A | 3/1995 | Mittelmeier et al. | |
| 5,397,364 A | 3/1995 | Kozak et al. | |
| 5,425,772 A | 6/1995 | Brantigan | |
| 5,435,723 A | 7/1995 | O'Brien | |
| 5,443,514 A | 8/1995 | Steffee | |
| 5,458,638 A * | 10/1995 | Kuslich et al. | 623/17.11 |
| 5,489,307 A | 2/1996 | Kuslich et al. | |
| 5,489,308 A | 2/1996 | Kuslich et al. | |
| 5,571,109 A | 11/1996 | Bertagnoli | |
| 5,571,189 A | 11/1996 | Kuslich | |
| 5,645,084 A * | 7/1997 | McKay | 128/898 |
| 5,669,909 A | 9/1997 | Zdeblick et al. | |
| 5,683,463 A * | 11/1997 | Godefroy et al. | 623/17.16 |
| 5,766,252 A | 6/1998 | Henry et al. | |
| 5,782,919 A * | 7/1998 | Zdeblick et al. | 623/17.16 |
| D397,439 S | 8/1998 | Koros et al. | |
| 5,800,547 A | 9/1998 | Schafer et al. | |
| 5,906,616 A | 5/1999 | Pavlov et al. | |
| 6,118,043 A * | 9/2000 | Nies et al. | 623/23.56 |

FOREIGN PATENT DOCUMENTS

| | | |
|---|---|---|
| DE | 24 46 039 | 4/1975 |
| DE | 26 46 039 | 4/1975 |
| DE | 29 10 627 | 9/1980 |
| DE | 3101333 A1 | 12/1981 |
| DE | 3132520 A1 | 6/1982 |
| DE | 3505567 A1 | 6/1986 |
| DE | 36 08 163 A1 | 9/1987 |
| DE | 41 04 359 A1 | 8/1992 |
| DE | 43 02 397 A1 | 7/1993 |
| EP | 0 077 159 | 4/1983 |
| EP | 0 162 005 | 11/1985 |
| EP | 0 179 695 | 4/1986 |
| EP | 0 260 044 | 3/1988 |
| EP | 0303241 A2 | 2/1989 |
| EP | 0 307 241 | 3/1989 |
| EP | 0499465 A1 | 8/1992 |
| EP | 0 551 187 A1 | 7/1993 |
| EP | 0551187 A1 | 7/1993 |
| EP | 0577179 A1 | 1/1994 |
| EP | 0 599 419 A2 | 6/1994 |
| EP | 0599419 A2 | 6/1994 |
| EP | 0 732 093 A2 | 9/1996 |
| ES | 283078 | 5/1985 |
| FR | 2 295 729 | 7/1976 |
| FR | 0 179 695 | 4/1986 |
| FR | 2 581 336 | 11/1986 |
| FR | 2 703 580 | 10/1994 |
| FR | 2 742 044 | 6/1997 |
| GB | 1291470 | 10/1972 |
| GB | 1492990 | 11/1977 |
| GB | 1531487 | 11/1978 |
| GB | 2076657 A | 12/1981 |
| GB | 2 083 754 | 3/1982 |
| GB | 2082754 A | 3/1982 |
| GB | 2126094 A | 3/1984 |
| GB | 2164277 A | 3/1986 |
| JP | 57-29348 | 2/1982 |
| JP | 60-31706 | 2/1985 |
| JP | 60-43984 | 3/1985 |
| JP | 61-122859 | 6/1986 |
| JP | 62-155846 | 7/1987 |
| SE | 106 101 | 7/1939 |
| SU | 1107854 | 8/1984 |
| SU | 1124960 | 11/1984 |
| SU | 1217374 | 3/1986 |
| SU | 1222254 | 4/1986 |
| WO | 84/01298 | 4/1984 |
| WO | 91/06266 | 5/1991 |
| WO | 92/14423 | 9/1992 |
| WO | 93/01771 | 2/1993 |

OTHER PUBLICATIONS

Cloward, Ralph B.; Ruptured Cervical Intervertebral Discs: Removal of Disc & Osteophytes & Anterior Cervical Interbody Fusion (A.C.I.F.); Codman; Signature Series 4.

Cloward, Ralph B.; Recent Advances in Surgery of the Cervical Spine; pp. 285-293; German Society For Neurosurgery: vol. 2 Cervical Spine Operations; Excerpta Medica.

Otero-Vich, Jose M.; Anterior Cervical Interbody Fusion with Threaded Cylindrical Bone; pp. 750-753; Journal of Neurosurgery, Nov. 1985, vol. 63, No. 5.

Hutter, Charles George; Spinal Stenosis and Posterior Lumbar Interbody Fusion; pp. 103-114; Clinical Orthopaedics and Related Research; No. 193; The Association of Bone and Joint Surgeons.

Lin, Paul M.; Posterior Lumbar Interbody Fusion; pp. 114-122; Charles C. Thomas; Springfield, Illinois.

Lin, Paul M.; Lumbar Interbody Fusion: Principles and Techniques in Spine Surgery; Techniques and Complications; pp. 81,98,120,146,173,180-184, 204, 224, 225, 231; Aspen Publishers, Inc.; 1989.

Tan, S.B.; A Modified Technique of Anterior Lumbar Fusion with Femoral Cortical Allograft; pp. 83-93; The Journal of Orthopaedic Surgical Techniques, vol. 5, No. 3, 1990.

Muller, M.E.; Manual of Internal Fixation: Techniques Recommended by the AO Group; Second Edition, Expanded and Revised; pp. 3-20, 27-41, 53-58, 71-78, 94, 311, 320; Springer-Verlag; 1979.

Hierholzer, G.; Manual on the AO/ASIF Tubular External Fixator; pp. 85-91; Springer-Verlag; 1985.

Heim, Urs; Small Fragment Set Manual: Technique Recommended by the ASIF-Group; pp. 5-7, 10, 20, 21, 30; Springer-Verlag: 1974.

Harmon, Paul H.; Anterior Excision and Vertebral Body Fusion Operation for Intervertebral Disk Syndromes of the Lower Lumbar Spine: Three- to Five-Year Results in 244 Cases; pp. 107-127; Clinical Orthopaedics and Related Research, No. 26, J.B. Lippincott Compnay, 1963.

Harmon, Paul H.; A Simplified Surgical Technic for Anterior Lumbar Diskectomy and Fusion; Avoidance of Complications; Anatomy of the Retroperitoneal Veins; pp. 130-143; Clinical Orthopaedics and Related Research, No. 37, J.B. Lippincott Company, 1964.

Bullough, Peter G.; Atlas of Spinal Diseases; Figure 5.7; J.B. Lippencott Company; 1988.

Butts, M.K.; Biomechanical Analysis of a New Method for Spinal Interbody Fixation; 1987 Symposium, American Society of Mechanical Engineers, "Advance in Bioengineering", Boston, MA (Dec. 13-18, 1987).

Canale, S. Terry; Campbell's Operative Orthopaedics; Vol. 3, 9th Edition; pp. 2191, 2216, 2459; Mosby, 1998.

Adams, et al.; Outline of Orthapaedics, Eleventh Edition; Trunk and Spine, p. 194.

Herkowitz, et al.; Principles of Bone Fusion; The Spine, Third Edition; Chapter 44, p. 1739.

Muschler, et al.; The Biology of Spinal Fusion; Spinal Fusion Science and Technique, Cotler and Cotler, pp. 9-13.

Zindrick, et al.; Lumbar Spine Fusion: Different Types and Indications; The Lumbar Spine, vol. 1, Second Edition, pp. 588-593 (1996).

Gillingham, F.J., et al.; Automatic Patient Monitoring in the Ward; Brit. J. Surg., vol. 53, No. 10, pp. 864-866 (Oct. 1966).

Maloney, A.F.J., et al.; Clinical and Pathological Observations in Fatal Head Injuries, Brit. J. Surg., vol. 56, No. 1, pp. 23-31 (Jan. 1969).

Harris, P., et al.; Spinal Deformity After Spinal Cord Injury; Paraplegia, vol. 6, No. 4, pp. 232-238 (Feb. 1969).

Gillingham, F.J., et al.; Head Injuries; Proceedings of the 18th World Congress of the International College of Surgeons, Rome, pp. 68-71 (May 28-31, 1972).

Whatmore, W. J.; Sincipital Encephalomeningoceles; Brit. J. Surg., vol. 60, No. 4, pp. 261-270 (Apr. 1973).

Whatmore, W. J.; Meningioma Following Trauma; Brit, J. Surg., vol. 60, No. 6, pp. 496-498 (Jun. 1973).

Bagby, George W.; Wobbler Syndrome in Horses (the Ataxic Horse); Spokane County Medical Society Bulletin; Spring 1979.

Rathke, F.W., et al.; Surgery of the Spine; Atlas of Orthopaedic Operations, vol. 1, p. 137, W.B. Saunders Co., Philadelphia (1979).

Albrektsson, T., et al.; Osseointegrated Titanium Implants; Acta. Orthop. Scand.; vol. 52:155-170 (1981).

Raveh, J., et al.; Neue Rekonstruktionsmoglichkeiten des Unterkiefers bei knochernen Defekten nach Tumorresektionen; Der Chirurg vol. 53:459-467 (1982).

Crock, H. V.; Practice of Spinal Surgery; Springer-Verlag/Wien, New York (1983).

Debowes, R.M., et al.; Study of Bovine . . . Steel Baskets; Transactions of the 29th Annual Meeting; Orthopaedic Reseach Society, vol, 8, p. 407, Mar. 8-10, 1983.

O'Neill, P., et al.; Spinal Meningoceles in Association with Neurofibromatosis; Neurosurgery, vol. 13, No. 1, pp. 82-84 (Jul. 1983).

Brandt, L., et al.; A Dowel Inserter for Anterior Cervical Interbody Fusion; J. Neurosurg. 61:793-794 (Oct. 1984).

Whatmore, W.J., et al.; The Conventry Cervical Spreader and Dowel Inserter; ACTA Neurochirurgica, vol. 70, FASC. 1-2 (1984).

Raveh, J., et al.; Use of the Titanium-coated Hollow Screw and Reconstruction Plate System in Bridging of Lower Jaw Defects; J. Oral Maxillofac Surg. 42:281-294 (1984).

Otero-Vich, Jose M.; Anterior Cervical Interbody Fusion with Threaded Cylindrical Bone; J. Neurosurg 63:750-753 (Nov. 1985).

Morscher, E., et al.; Die vordere Verplattung der Halswirbelsäule mit dem Hohlschrauben-Plattensystem aus Titanium, *Der Chirurg*, vol. 57, pp. 702-707 (1986) with English Translation.

Bagby, G.W.; Basket Implant Facilitates Spinal Fusion; Orthopedics Today, vol. 7, No. 10, (Oct. 1987).

Butts, M. K., et al.; Biomechanical Analysis of a New Method for Spinal Interbody Fixation; 1987 Symposium, American Society of Mechanical Engineers, "Advances in Bioengineering", Boston, MA (Dec. 13-18, 1987).

Crawley et al.; A Modified Cloward's Technique for Arthrodesis of the Normal Metacarpophalangeal Joint in the Horse; Veterinary Surgery, vol. 17, No. 3, pp. 117-127 (1988).

Raveh, J., et al.; Surgical Procedures for Reconstruction of the Lower Jaw Using the Titanium-Coated Hollow-Screw Reconstruction Plate System: Bridging of Defects; Otolaryngologic Clinics of North America; vol. 20, No. 3 (Aug. 1987).

Whatmore, W. J.; Proceedings of the Society of British Neurological Surgeons; Journal of Neurology, Neurosurgery, and Psychiatry, 50:1093-1100 (1987).

Goldthwaite, N., et al.; Toward Percutaneous Spine Fusion; Ch. 45; Lumbar Spine Surgery; C.V. Mosby Company, pp. 512-522 (1987).

Bagby, G.W.; Arthrodesis by the Distraction-Compression Method Using a Stainless Steel Implant; Orthopedics, vol. II, No. 6, pp. 931-934 (Jun. 1987).

Itoman, M., et al.; Banked Bone Grafting for Bone Defect Repair—Clinical Evaluation of Bone Union and Graft Incorporation; J. Jpn. Orthop. Assoc. 62:461-469 (1988).

Kane, W.J.; Direct Current Electrical Bone Growth Stimulation for Spinal Fusion; Spine, vol. 13, No. 3, pp. 363-365 (Mar. 1988).

The SpF-T Spinal Fusion Stimulator: An Efficacious Adjunct that Meets the Diverse Needs of Spine Patients; EBI Medical Systems; (Aug. 1991).

Schmitz et al.; Performance of Alloplastic Materials and Design of an Artificial Disc; The Artificial Disc, Brock, Mayer, Weigel; pp. 23-34 (1991).

The Use of Direct Current for Electrically Induced Osteogenesis; The Positive Effect of an Electronegative charge on Bone Growth; EBI Medical Systems (Feb. 1993).

Mylonas, C., et al.; Anterior Cervical Decompression and Fusion Using the Coventry Cervical Spreader and Dowel Inserter; British Journal of Neurosurgery, 7:545-549 (1993).

Fusion of the Lumbar Spine; Anterior Monosegmental Fusion L5-S1, Atlas of Spinal Operations, Thieme, pp. 270-274 (1993).

Spine Basics, Danek Group, Inc., Glossary (1993).

Lumbar Spine Surgery, Techniques & Complications; History of Lumbar Spine Surgery (1994) pp. 11-15; 27; 30; 35-45; 265-268.

* cited by examiner

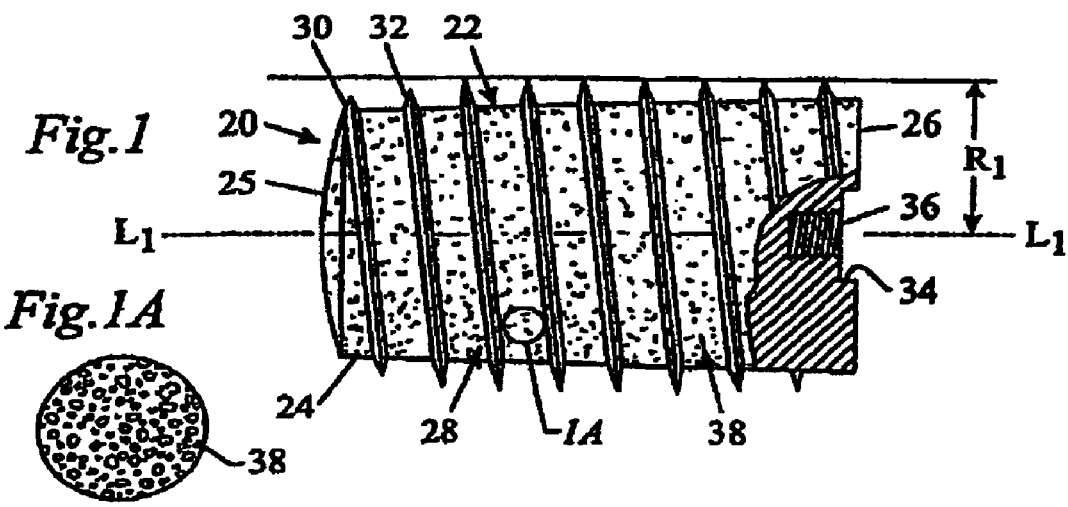
Fig.1
Fig.1A
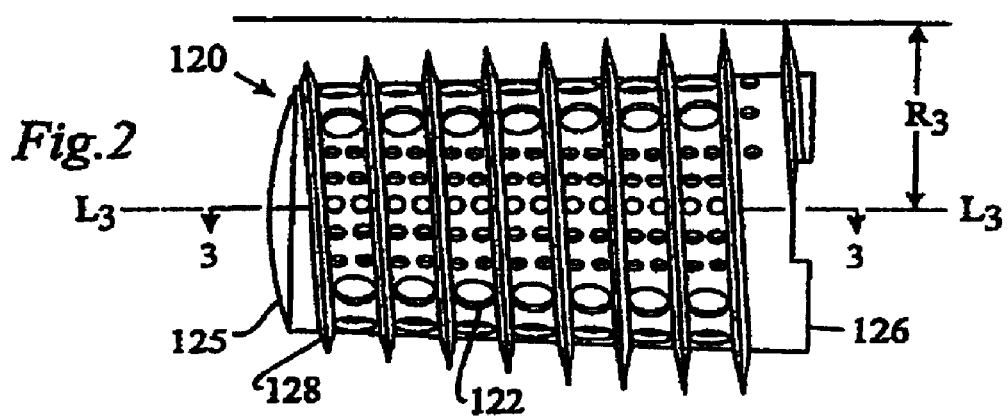
Fig.2
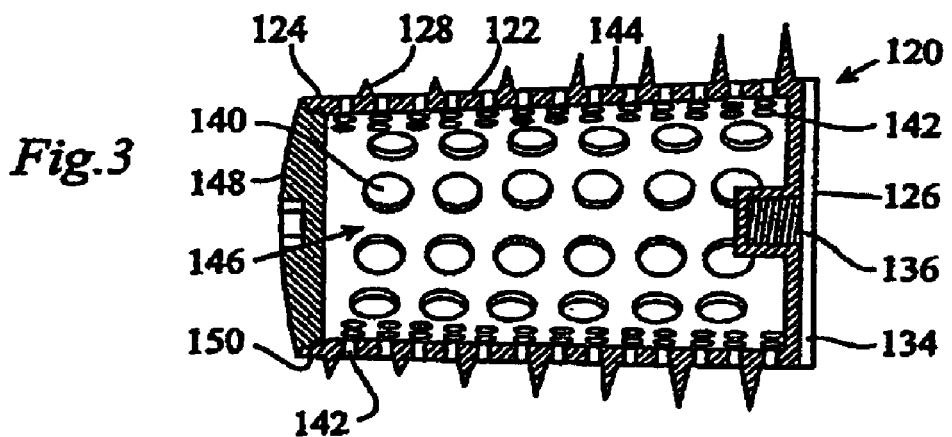
Fig.3

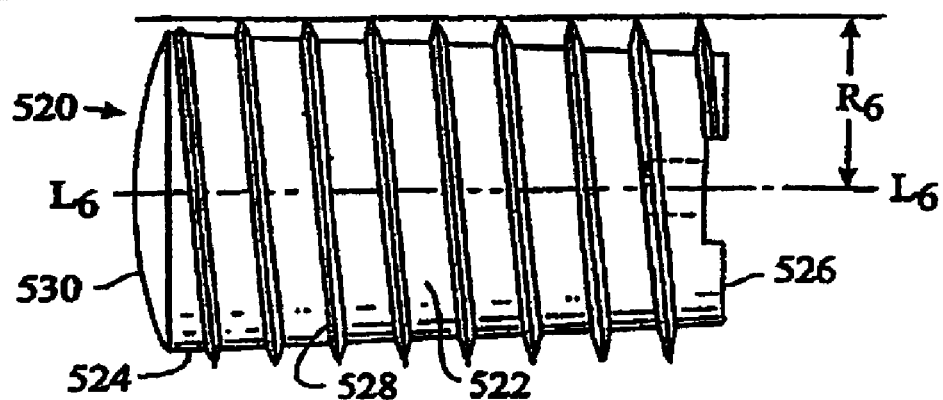
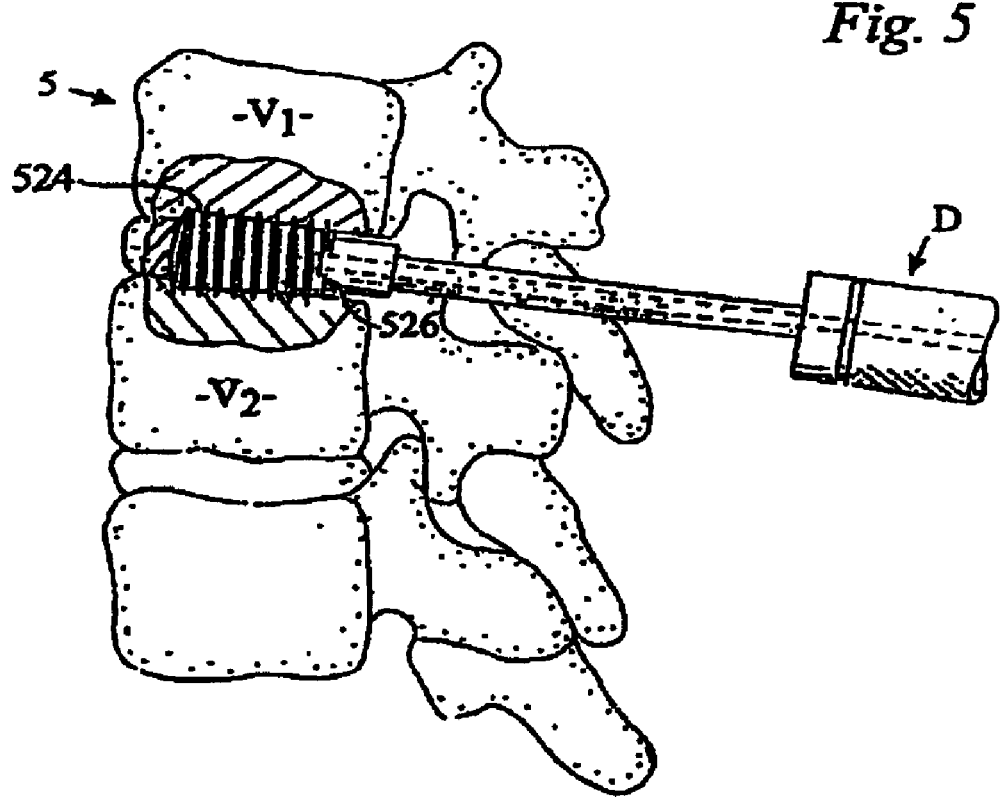

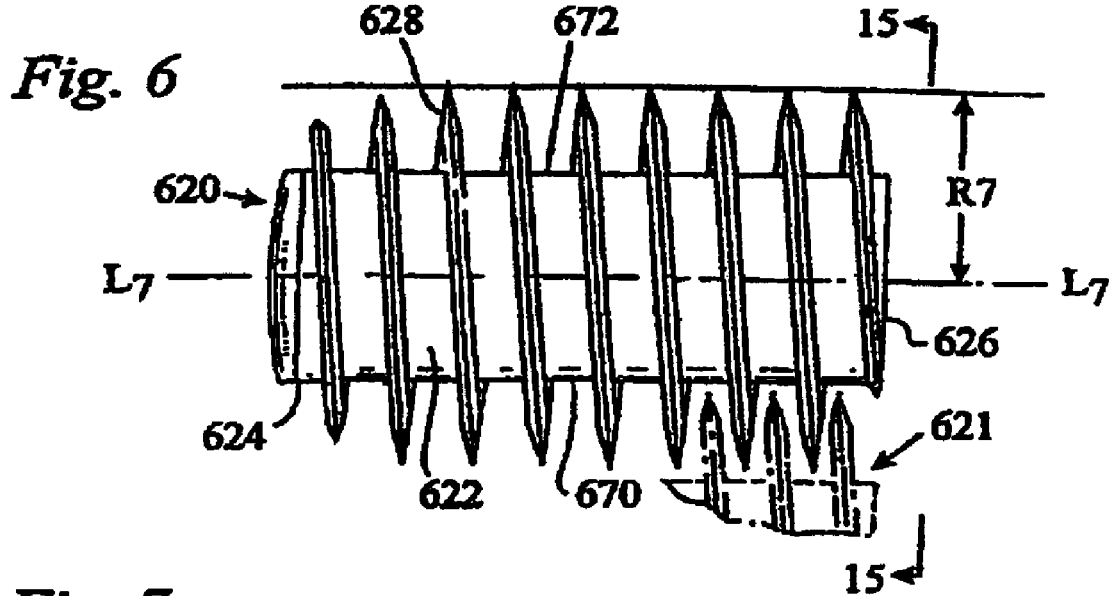
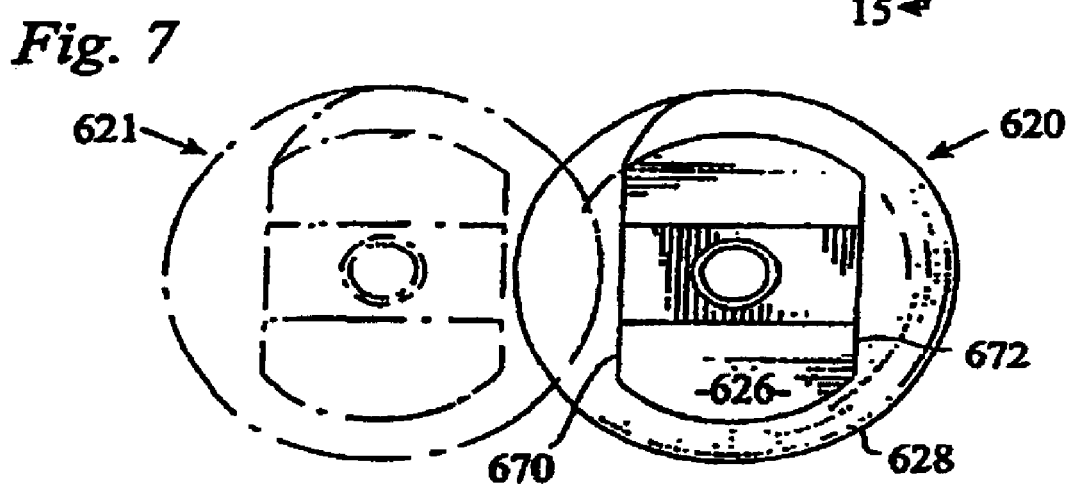
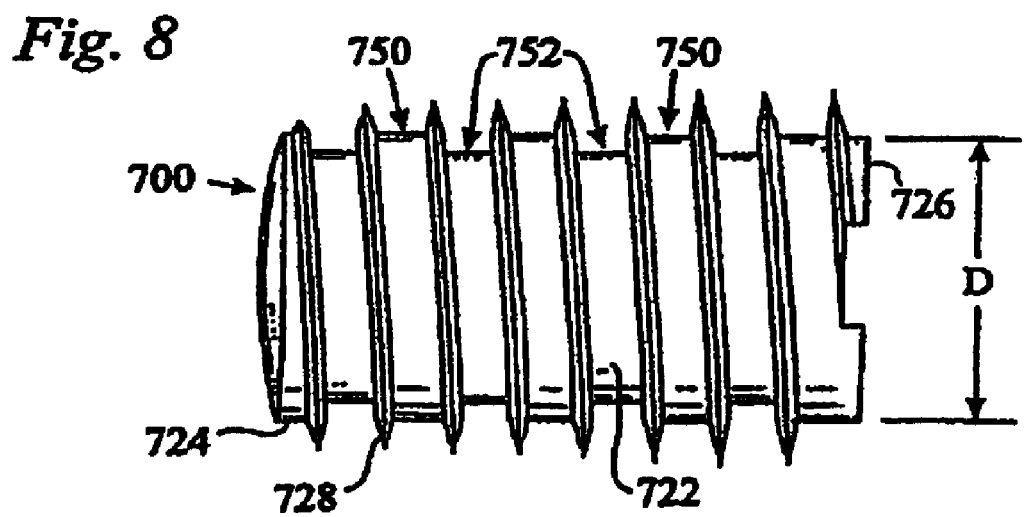

THREADED FRUSTO-CONICAL INTERBODY SPINAL FUSION IMPLANTS

RELATED APPLICATIONS

This application is a continuation in part of U.S. application Ser. No. 08/396,414 filed on Feb. 27, 1995 now U.S. Pat. No. 6,080,155, which is a continuation-in-part of U.S. application Ser. No. 08/074,781 filed on Jun. 10, 1993, now U.S. Pat. No. 5,484,437, which is a continuation in part of U.S. application Ser. No. 07/968,240 filed on Oct. 29, 1992, which is a continuation of U.S. application Ser. No. 07/698,674 filed on May 10, 1991 now abandoned which is a divisional of application Ser. No. 07/205,935 filed on Jun. 13, 1988, now U.S. Pat. No. 5,015,247, all of which are incorporated herein by reference.

This application is also a continuation-in-part of U.S. application Ser. No. 08/390,131 entitled Interbody Spinal Fusion Implants filed on Feb. 17, 1995 now U.S. Pat. No. 5,593,409.

BACKGROUND OF THE INVENTION

1. Field of the Invention

The present invention relates generally to interbody spinal fusion implants, and in particular to spinal fusion implants configured to restore and maintain two adjacent vertebrae of the spine in anatomical lordosis.

2. Description of the Related Art

Interbody spinal fusion refers to the method of achieving bony bridging between adjacent vertebrae through the disc space, the space between adjacent vertebrae normally occupied by a spinal disc. Numerous implants to facilitate such a fusion have been described by Cloward, Brantigan, and others, and are known to those skilled in the art. Generally, cylindrical implants offer the advantage of conforming to an easily prepared recipient bore spanning the disc space and penetrating into each of the adjacent vertebrae. Such a bore may be created by use of a drill. It is an anatomical fact that both the cervical spine and the lumbar spine are normally lordotic, that is convex forward. Such alignment is important to the proper functioning of the spine. Commonly, those conditions which require treatment of spinal fusion are associated with a loss of lordosis.

Therefore, there exists a need for spinal fusion implants that permit for the restoration of anatomical lordosis.

SUMMARY OF THE INVENTION

The present invention is directed to a variety of interbody spinal fusion implants having at least a partially frusto-conical configuration. In the preferred embodiment, the spinal fusion implants of the present invention have a body that is partially or fully frusto-conical shape substantially along the portion of the implant in contact with the adjacent vertebrae of the spine. The spinal fusion implants of the present invention have an external thread for engaging the adjacent vertebrae of the spine and have an insertion end and a trailing end. The external thread may have a variable or constant thread radius and/or a constant or variable thread height measured from the body of the implant.

The spinal fusion implants of the present invention may be further modified so that while the upper and lower surfaces are portions of a frusto-cone, at least one side portion may be truncated to form a planar surface that is parallel to the central longitudinal axis of the implant to form straight walls. These implants may have a more tapered aspect at the insertion end of the implant to facilitate insertion. The spinal fusion implants of the present invention may be relatively solid and/or porous and/or hollow, and may have surface roughenings to promote bone ingrowth and stability.

The spinal fusion implants of the present invention may have wells extending into the material of the implant from the surface for the purpose of holding fusion promoting materials and to provide for areas of bone ingrowth fixation. These wells, or holes, may pass either into or through the implant and may or may not intersect. The spinal fusion implants of the present invention may have at least one chamber which may be in communication through at least one opening to the surface of the implant. Said chamber may have at least one access opening for loading the chamber with fusion promoting substances. The access opening may be capable of being closed with a cap or similar means.

The spinal fusion implants of the present invention offer significant advantages over the prior art implants:

1. Because the signal fusion implants of the present invention are at least partially frusto-conical in shape, those that taper from the leading edge to the trailing edge are easy to introduce and easy to fully insert into the spinal segment to be fused. In another embodiment, where the trailing edge of the implant is larger than the leading edge, the implant utilizes a tapered forward portion and an increasing thread height relative to the body from the leading edge to the trailing edge to facilitate insertion.
2. The shape of the implants of the present invention is consistent with the shape of the disc, which the implants at least in part replace, wherein the front of the disc is normally taller than the back of the disc, which allows for normal lordosis. The implants of the present invention are similarly taller anteriorly than they are posteriorly.
3. The spinal fusion implants of the present invention conform to a geometric shape, which shape is readily producible at the site of fusion, to receive said spinal fusion implants.

The spinal fusion implants of the present invention can be made of any material appropriate for human implantation and having the mechanical properties sufficient to be utilized for the intended purpose of spinal fusion, including various metals such as cobalt chrome, stainless steel or titanium including its alloys, various plastics including those which are bioabsorbable, and various ceramics or combination sufficient for the intended purpose. Further, the spinal fusion implants of the present invention may be made of a solid material, a mesh-like material, a porous material and may comprise, wholly or in part, materials capable of directly participating in the spinal fusion process, or be loaded with, composed of, treated or coated with chemical substances such as bone, morphogenic proteins, hydroxyapatite in any of its forms, and osteogenic proteins, to make them bioactive for the purpose of stimulating spinal fusion. The implants of the present invention may be wholly or in part bioabsorbable.

OBJECTS OF THE PRESENT INVENTION

It is an object of the present invention to provide a spinal fusion implant that is easily inserted into the spine, having a tapered leading end;

It is another object of the present invention to provide a spinal fusion implant that tapers in height from one end to the other consistent with the taper of a normal spinal disc;

It is yet another object of the present invention to provide a spinal fusion implant that is capable of maintaining anatomic alignment and lordosis of two adjacent vertebrae during the spinal fusion process;

It is still another object of the present invention to provide a spinal fusion implant that is self stabilizing within the spine;

It is yet another object of the present invention to provide a spinal fusion implant that is capable of providing stability between adjacent vertebrae when inserted;

It is still another object of the present invention to provide a spinal fusion implant that is capable of participating in the fusion process by containing, being composed of, or being treated with fusion promoting substances;

It is further another object of the present invention to provide a spinal fusion implant that is capable of spacing apart and supporting adjacent vertebrae during the spinal fusion process;

It is still further another object of the present invention to provide a spinal fusion implant that is consistent in use with the preservation of a uniform thickness of the subchondral vertebral bone;

It is another object of the present invention to provide a spinal fusion implant having a shape which conforms to an easily produced complementary bore at the fusion site; and It is a further object of the present invention to provide a frusto-conical spinal fusion implant which may be placed side by side adjacent to a second identical implant across the same disc space, such that the combined width of the two implants is less than sum of the individual heights of each implant.

It is a further object of the present invention to provide a frusto-conical spinal fusion implant which may be placed side by side adjacent to a second identical implant across the same disc space, such that the combined width of the two implants is less than sum of the individual lengths of each implant.

These and other objects of the present invention will become apparent from a review of the accompanying drawings and the detailed description of the drawings.

BRIEF DESCRIPTION OF THE DRAWINGS

FIG. 1 is a side elevational view of the spinal fusion implant of the present invention having a body that is frusto-conical with an external thread having a substantially uniform radius.

FIG. 1A is an enlarged fragmentary view along line 1A of FIG. 1 illustrating the surface configuration of the implant of FIG. 1.

FIG. 2 is an alternative embodiment of the spinal fusion implant of the present invention having a frusto-conical body with an external thread radius and thread height that are not constant.

FIG. 3 is as cross sectional view along line 3-3 of the implant of FIG. 2.

FIG. 4 is a side elevational view of an alternative embodiment of the spinal fusion implant of the present invention.

FIG. 5 is a side elevational view and partial cut-away of a segment of the spinal column in lordosis showing the spinal fusion implant of FIG. 4 being implanted with a driving instrument from the posterior approach to the spinal column.

FIG. 6 is a side elevational view of an alternative embodiment of the spinal fusion implant of the present invention having a frusto-conical body and truncated sides.

FIG. 7 is an end view along line 7-7 of the spinal fusion implant of FIG. 6 shown placed beside a second identical implant shown in hidden line.

FIG. 8 is a side elevational view of an alternative embodiment of the spinal fusion implant of the present invention having a body with an irregular configuration.

DETAILED DESCRIPTION OF THE DRAWINGS

Figure 1B:
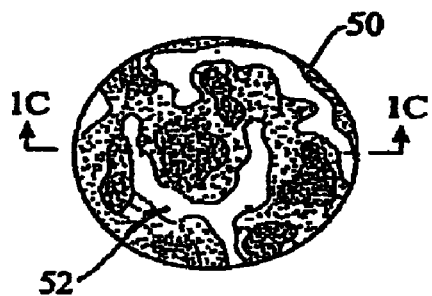
FIG. 1B is an enlarged fragmentary view along line 1A of FIG. 1 illustrating an alternative embodiment of the surface configuration of the implant of the present invention made of a cancellous material.
Figure 1C:
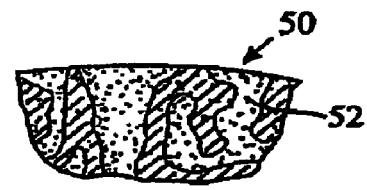
FIG. 1C is a cross sectional view along lines 1C-1C of FIG. 1B illustrating the alternative embodiment of the surface configuration of the implant of the present invention made of a cancellous material.

Referring to FIG. 1, a side elevational view of the spinal fusion implant of the present invention generally referred to by numeral 20 is shown. The implant 20 has a body 22 that is frusto-conical in shape such that the body 22 has a diameter (root diameter) that is generally frusto-conical. The body 22 has an insertion end 24 and a trailing end 26. The insertion end 24 may include a tapered portion 25 to facilitate insertion of the spinal implant 20. In the preferred embodiment, when the implant 20 is inserted from the anterior aspect of the spine, the body 22 of the implant 20 has a maximum diameter at a point nearest to the trailing end 26 and a minimum diameter at a point nearest to the insertion end 24.

The implant 20 has an external thread 28 having a substantially uniform radius $R_1$ measured from the central longitudinal axis $L_1$ of the implant 20. The outer locus of the external thread 28 (major diameter) has an overall configuration that is substantially parallel to the longitudinal axis $L_1$. While the major diameter of the implant 20 is substantially uniform, the external thread 28 may be modified at the leading edge by having initially a reduced thread radius to facilitate insertion of the implant 20 and may also be modified to make the external thread 28 self-tapping. In the preferred embodiment, the external thread 28 has a first thread 30 of a lesser radius than the radius $R_1$ of the remainder of the external thread 28 to facilitate insertion of the implant 20. The second thread 32 has a greater radius than the first thread 30, but is still shorter than the radius $R_1$ of the remainder of the external thread 28 which is thereafter of constant radius.

The body 22 is frusto-conical substantially along the portion of the body 22 in contact with the adjacent vertebrae of the spine which allows for creating and maintaining the adjacent vertebrae of the spine in the appropriate angular relationship to each other in order to preserve and/or restore the normal anatomic lordosis of the spine. The substantially uniform radius $R_1$ of the external thread 28 of the implant 20 allows engaging the bone of the adjacent vertebrae in a position that counters the forces which tend to urge the implant 20 from between the adjacent vertebrae in the direction opposite to which the implant 20 was implanted. The greater thread height measured from the body 22 near the leading end 24 of the implant 20 provides greater purchase into the vertebral bone and again enhances the stability of the implant 20.

Further, the configuration of the external thread 28 increases the surface area of the implant 20 in contact with the vertebrae to promote bone ingrowth.

The implant 20 has a recessed slot 34 at its trailing end 26 for receiving and engaging insertion instrumentation for inserting the implant 20. The recessed slot 34 has a threaded opening 36 for threadably attaching the implant 20 to instrumentation used for inserting the implant 20.

Referring to FIG. 1A, the implant 20 has an outer surface 38 that is porous to present an irregular surface to the bone to promote bone ingrowth. The outer surface 38 is also able to hold fusion promoting materials and provides for an increased surface area to engage the bone in the fusion process and to provide further stability. The pores of the outer surfaces 38 are microscopic in size having a diameter that is less than 1 mm, in the range of 50-1000 microns, with 250-500 microns being the preferred diameter. It is appreciated that the outer surface 38, and/or the entire implant 20, may comprise any other porous material or roughened surface sufficient to hold fusion promoting substances and/or allow for bone ingrowth and/or engage the bone during the fusion process. The implant 20 may be further coated with bioactive fusion promoting substances including, but not limited to, hydroxyapatite compounds, osteogenic proteins and bone morphogenic proteins. The implant 20 is shown as being solid, however it is appreciated that it can be made to be substantially hollow or hollow in part.

Referring to FIG. 1B, an enlarged fragmentary view along line 1A of FIG. 1 illustrating an alternative embodiment of the surface configuration 38 of the implant of the present invention made of a cancellous material is shown. The cancellous material 50, similar in configuration to human cancellous bone, having interstices 52 such that the outer surface 38 has a configuration as shown in FIGS. 1B and 1C. As the implant of the present invention may be made entirely or in part of the cancellous material 50, the interstices 52 may be present in the outer surface 338 and/or within the entire implant to promote bone ingrowth and hold bone fusion promoting materials.

Figure 1D:
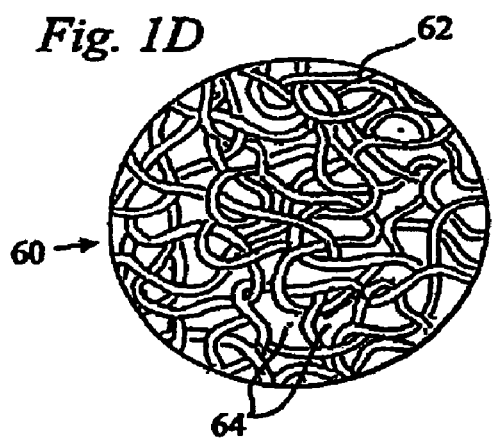
FIG. 1D is an enlarged fragmentary view along line 1A of FIG. 1 illustrating an alternative embodiment of the surface configuration of the implant of the present invention made of a fibrous mesh-like material.

Referring to FIG. 1D, an enlarged fragmentary view along line 1A of FIG. 1 illustrating an alternative embodiment of the surface configuration of the implant of the present invention made of a fibrous mesh-like material is shown. The mesh-like material 60 comprises strands 62 that are formed and pressed together such that interstices 64, capable of retaining fusion promoting material and for allowing for bone ingrowth, are present between the strands in at least the outer surface 38 of implant of the present invention.

Figure 1E:
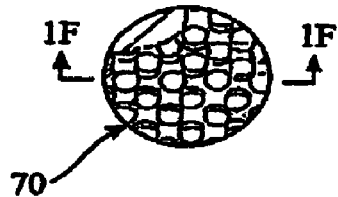
FIG. 1E is a fragmentary view along line 1A of FIG. 1 illustrating an alternative embodiment of the surface configuration of the implant of the present invention comprising a plurality of spaced apart posts.
Figure 1F:
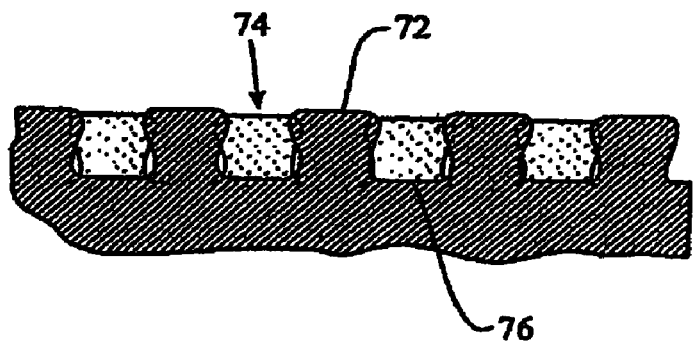
FIG. 1F is an enlarged fragmentary sectional view along lines 1F-1F of FIG. 1E illustrating the surface configuration of the implant of FIG. 1E.

Referring to FIGS. 1E and 1F, a fragmentary view along line 1A of FIG. 1 illustrating an alternative embodiment of the surface configuration 38 of the implant of the present invention comprising a plurality of spaced apart posts 70 is shown. The posts 70 have a head portion 72 of a larger diameter than the remainder of the posts 70, and each of the interstices 74 is the reverse configuration of the posts 72, having a bottom 76 that is wider than the entrance to the interstices 74. Such a configuration of the posts 70 and interstices 74 aids in the retention of bone material in the surface 38 of the implant and further assists in the locking of the implant into the bone fusion mass created from the bone ingrowth. As the bone ingrowth at the bottom 76 of the interstices is wider than the entrance, the bone ingrowth cannot exit from the entrance and is locked within the interstice 74. The surface of the implant provides for an improvement in the available amount of surface area which may be still further increased by rough finishing, flocking or otherwise producing a non smooth surface.

In the preferred embodiment, the posts 70 have a maximum diameter in the range of approximately 0.1-2 mm and a height of approximately 0.1-2 mm and are spaced apart a distance of approximately 0.1-2 mm such that the interstices 74 have a width in the range of approximately 0.1 to 2 mm. The post sizes, shapes, and distributions may be varied within the same implant.

In the preferred embodiment, for use in the lumbar spine, the implant 20 has an overall length in the range of approximately 24 mm to 32 mm with 26 mm being the preferred length. The body 22 of the implant 20 has a root diameter at the insertion end 24 in the range of 8-20 mm, with 14-16 mm being the preferred root diameter at the insertion end, and a root diameter at the trailing end 26 in the range of 10-24 mm, with 16-18 mm being the preferred diameter at the trailing end 26, when said implants are used in pairs. When used singly in the lumbar spine, the preferred diameters would be larger.

In the preferred embodiment, the implant 20 has a thread radius $R_1$ in the range of 6 mm to 12 mm, with 9-10 mm being the preferred radius $R_1$. For use in the cervical spine, the implant 20 has an overall length in the range of approximately 10-22 mm, with 12-14 mm being the preferred length. The body 22 of the implant 20 has a root diameter at the insertion end 24 in the range of 8-22 mm, with 16-18 mm being the preferred root diameter at the insertion end when used singly, and 8-10 mm, when used in pairs. The body 22 of the implant 20 has a root diameter at the trailing end 26 in the range of 10-24 mm, with 18-20 mm being the preferred root diameter at the trailing end 26 when used singly, and 10-12 mm when used in pairs; a thread radius $R_1$ in the range of approximately 4-12 mm, with 9-10 mm being the preferred radius $R_1$ when inserted singularly and 5-7 mm when inserted side by side in pairs.

Referring to FIG. 2, an alternative embodiment of implant 20 is shown and generally referred to by the numeral 120. The implant 120 has a body 122 similar to body 122 of implant 120 and has an external thread 128 having a radius $R_3$ measured from the central longitudinal axis $L_3$ of the implant 120. The thread radius $R_3$ is not constant throughout the length of the implant 120 and the external thread 128 has a thread height that is also not constant with respect to the body 122 of the implant 120. In the preferred embodiment, the implant 120 has an external thread 128 with a radius $R_3$ that increases in size from the insertion end 124 to the trailing end 126 of the implant 120.

Referring to FIG. 3, a cross sectional view along line 3-3 of the implant 120 is shown. The implant 120 has an outer wall 144 surrounding an internal chamber 146. The large and small openings 140 and 142 may pass through the outer wall 144 to communicate with the internal chamber 146. The internal chamber 146 may be filled with bone material or any natural or artificial bone growth material or fusion promoting material such that bone growth occurs from the vertebrae through the openings 140 and 142 to the material within internal chamber 146. While the openings 140 and 142 have been shown in the drawings as being circular, it is appreciated that the openings 140 and 142 may have any shape, size configuration or distribution, suitable for use in a spinal fusion implant without departing from the scope of the present invention.

The openings 140 and 142 are macroscopic in size having a diameter that is greater than 1 mm. The large openings 140 have a diameter in the range of 206 mm, with the preferred diameter being 3.5 mm; and the small openings have a diameter in the range of 1-2 mm, with 1.5 mm being the preferred diameter.

The implant 120 has a cap 148 with a thread 150 that threadably attaches to the insertion end 124 of the spinal fusion implant 120. The cap 148 is removable to provide access to the internal chamber 146, such that the internal chamber 146 can be filled and hold any natural or artificial osteoconductive, osteoinductive, osteogenic, or other fusion enhancing material. Some examples of such materials are bone harvested from the patient, or bone growth inducing material such as, but not limited to, hydroxyapatite, hydroxyapatite tricalcium phosphate; or bone morphogenic protein. The cap 148 and/or the spinal fusion implant 120 may be made of any material appropriate for human implantation including metals such as cobalt chrome, stainless steel, titanium, plastics, ceramics, composites and/or may be made of, and/or filled, and/or coated with a bone ingrowth inducing material such as, but not limited to, hydroxyapatite or hydroxyapatite tricalcium phosphate or any other osteoconductive, osteoinductive, osteogenic, or other fusion enhancing material. The cap 148 and the implant 120 may be partially or wholly bioabsorbable.

Referring to FIG. 4, a side elevational view of an alternative embodiment of the spinal fusion implant of the present invention generally referred to by numeral 520 is shown. The implant 520 has a body 522 having a root diameter that is frusto-conical in the reverse direction as that of implant 20 shown in FIG. 1, in order to preserve and/or restore lordosis in a segment of spinal column when inserted from the posterior aspect of the spine. The body 522 has an insertion end 524 and a trailing end 526. In the preferred embodiment, the body 522 of the implant 520 has a minimum diameter at a point nearest to the trailing end 526 and a maximum diameter at a point nearest to the insertion end 524. The insertion end 524 may have an anterior nose cone portion 530 presenting a tapered end to facilitate insertion.

The implant 520 has an external thread 528 having a substantially uniform radius $R_6$ measured from the central longitudinal axis $L_6$ of the implant 520, such that the external diameter of the external thread 528 (major diameter) has an overall configuration that is substantially parallel to the longitudinal axis $L_6$. It is appreciated that the thread 528 can have a major diameter that varies with respect to the longitudinal axis $L_6$, such that the major diameter may increase from the insertion end 524 to the trailing end 526 or the reverse. The external thread 528 has a thread height measured from the body 522 that increases from the insertion end 524 to the trailing end 526.

Referring to FIG. 5, a segment of the spinal column S is shown with the vertebrae $V_1$ and $V_2$ in lordosis and an implant 520 shown being inserted from the posterior aspect of the spinal column S with an instrument driver D. The implant 520 is inserted with the larger diameter insertion end 524 first in order to in initially distract apart the vertebrae $V_1$ and $V_2$ which then angle toward each other posteriorly as the implant 520 is fully inserted. It is appreciated that the insertion of implant 520 does not require the adjacent vertebrae $V_1$ and $V_2$ to be placed in lordosis prior to insertion, as the full insertion of the implant 520 itself is capable of creating the desired lordotic angular relationship of the two vertebrae $V_1$ and $V_2$.

In the preferred embodiment, for use in the lumbar spine, the implant 520 has an overall length in the range of approximately 24 mm to 30 mm, with 26 mm being the preferred length. The body 522 of the implant 520 has a root diameter at the insertion end 524 in the range of 12-22 mm, with 16 mm being the preferred root diameter at the insertion end, and a root diameter at the trailing end 526 in the range of 10-20 mm, with 14 mm being the preferred diameter at the trailing end 526. In the preferred embodiment, the implant 520 has a thread radius $R_6$ in the range of 6 mm to 12 mm, with 8 mm being the preferred radius $R_6$.

Referring to FIG. 6, an alternative embodiment of the spinal fusion implant of the present invention generally referred to by the numeral 620 and a partial fragmentary view of a second identical implant, generally referred to by the numeral 621 are shown. The implant 620 has a body 622 that is partially frusto-conical in shape similar to body 22 of implant 20 shown in FIG. 1, and has an insertion end 624 and a trailing end 626. The body 622 of the implant 620 has truncated sides 670 and 672 forming planar surfaces that are parallel to the longitudinal axis $L_7$. In this manner, two implants 620 and 621 may be placed side by side, with one of the sides 670 or 672 of each implant with little space between them, such that the area of contact with the bone of the adjacent vertebrae is maximized. It is appreciated that the body 622 may also be cylindrical in shape and have truncated sides 670 and 672.

The implant 620 has an external thread 628 having a radius $R_6$ measured from the central longitudinal axis $L_7$ that may be constant, such that the major diameter or outer locus of the external thread 628 has an overall configuration that is substantially cylindrical. It is appreciated that the external thread 628 may have a thread radius $R_7$ that is variable with respect to the longitudinal axis $L_7$ such that the major diameter or outer locus of the external thread 628 has an overall configuration that is substantially frusto-conical.

Referring to FIG. 7, an end view of the implant 620 placed beside implant 621 is shown. The implant 620 has a thread radius that is substantially constant and has a thread height measured from the body 622 that is greater at the sides 670 and 672. In this manner, two implants 620 and 621 can be placed beside each other with the external thread 628 of each implant interdigitated allowing for closer adjacent placement of the two implants as a result of the substantial overlap of the external thread 628 at the side 670 or 672 of the implants.

Referring to FIG. 8, an alternative embodiment of the implant of the present invention is shown and generally referred to by the numeral 700. The implant 700 is similar in configuration to implant 20 shown in FIG. 1, except that the body 722 has an irregular configuration. The configuration of the body 722 has a root diameter D which is variable in size throughout the length of the implant 700 and, as shown in this embodiment, comprises larger diameter portions 750 and smaller diameter portions 752. It is appreciated that each of the large diameter portions 750 may be of the same or different diameter and each of the smaller diameter portions 752 may be of the same or different diameter.

The outer surface of the body 722 of implant 720 may be filled with fusion promoting substances such that the smaller diameter portions 752 may hold such fusion promoting substances. If so filled, the composite of the implant 700 and the fusion promoting material could still produce an even external surface of the body 722 if so desired.

While the present invention has been described in detail with regards to the preferred embodiments, it is appreciated that other variations of the present invention may be devised which do not depart from the inventive concept of the present invention. In particular, it is appreciated that the various teachings described in regards to the specific embodiments herein may be combined in a variety of ways such that the features are not limited to the specific embodiments described above.

Each of the features disclosed in the various embodiments and their functional equivalents may be combined in any combination sufficient to achieve the purposes of the present invention as described herein.

What is claimed is:

1. An interbody spinal fusion implant for insertion across a disc space between adjacent vertebral bodies of a human spine, said implant comprising a body having an insertion end, a trailing end, a length between said ends, and an outer surface including a thread for engaging said implant to the adjacent vertebral bodies, the outer locus of said thread forming a substantially frusto-conical configuration along at least a portion of the length of said implant nearer said trailing end than said insertion end.

2. The implant of claim 1 in which said body has a substantially frusto-conical configuration along a sufficient portion of said implant that is adapted to contact the adjacent vertebral bodies when implanted in the spine so as to maintain an angulation of the adjacent vertebral bodies relative to one another.

3. The implant of claim 1 in which said body has a substantially cylindrical configuration.

4. The spinal fusion implant of claim 1 in which said trailing end is larger than said insertion end.

5. The spinal fusion implant of claim 1 in which said insertion end is larger than said trailing end.

6. The spinal fusion implant of claim 1 in which said implant comprises a bone ingrowth material.

7. The spinal fusion implant of claim 1 in which said implant comprises a fusion promoting material.

8. The spinal fusion implant of claim 1 in which said implant is at least in part bioabsorbable.

9. The spinal fusion implant of claim 1 in which said body has a plurality of openings for retaining fusion promoting material.

10. The spinal fusion implant of claim 1 in which said thread has a thread radius measured from the longitudinal central axis of said implant, said thread radius being variable along the length of said implant.

11. The spinal fusion implant of claim 1 in which said thread has a thread height measured from said body which is variable along the length of said implant.

12. The spinal fusion implant of claim 1 in which said thread beyond said insertion end has a thread height measured from said body which is substantially constant along the length of said implant.

13. The spinal fusion implant of claim 1 in which said body comprises a porous material.

14. The spinal fusion implant of claim 1 in which said body has an internal chamber and a means for accessing said internal chamber.

15. The spinal fusion implant of claim 14 in which said internal chamber is capable of containing fusion promoting material.

16. The spinal fusion implant of claim 14 in which said body includes a wall surrounding said internal chamber.

17. The spinal fusion implant of claim 16 in which said wall has a plurality of openings passing therethrough in communication with said internal chamber.

18. The spinal fusion implant of claim 14 in which said body has means for closing said accessing means.

19. The spinal fusion implant of claim 15 in which said body has means for closing said accessing means.

20. The spinal fusion implant of claim 1 in which said implant includes an engagement means for engaging instrumentation for the insertion of said implant.

21. The spinal fusion implant of claim 1 in which at least a portion of said outer surface comprises wells having at least partial walls.

22. The spinal fusion implant of claim 1 in which said body has a longitudinal central axis and at least one truncated side forming a planar surface parallel to said central axis.

23. The spinal fusion implant of claim 22 in which said thread has a thread height measured from said body which is greatest at said truncated side.

24. An interbody spinal fusion implant for insertion across a disc space between two adjacent vertebral bodies of a human spine, said implant comprising a body having a substantially frusto-conical configuration along a sufficient portion of said body that is adapted to contact the adjacent vertebral bodies when implanted in the spine so as to maintain an angulation of the adjacent vertebral bodies relative to one another, said body having an insertion end, a trailing end, and an outer surface including a thread for engaging said implant to the adjacent vertebral bodies of the spine, the locus of said thread forming a substantially cylindrical configuration.

25. The spinal fusion implant of claim 24 in which said trailing end is larger than said insertion end.

26. The spinal fusion implant of claim 24 in which said insertion end is larger than said trailing end.

27. The spinal fusion implant of claim 24 in which said implant comprises a bone ingrowth material.

28. The spinal fusion implant of claim 24 in which said implant comprises a fusion promoting material.

29. The spinal fusion implant of claim 24 in which said implant is at least in part bioabsorbable.

30. The spinal fusion implant of claim 24 in which said body has a plurality of openings for retaining fusion promoting material.

31. The spinal fusion implant of claim 24 in which said thread beyond said insertion end has a thread radius measured from the longitudinal central axis of said implant, said thread radius being substantially uniform throughout the length of said implant.

32. The spinal fusion implant of claim 24 in which said thread has a thread radius measured from the longitudinal central axis of said implant, said thread radius being variable along at least a portion of said implant.

33. The spinal fusion implant of claim 24 in which said thread has a thread height measured from said body which is variable along the length of said implant.

34. The spinal fusion implant of claim 24 in which said thread has a thread height measured from said body which is substantially constant along at least a portion of said implant.

35. The spinal fusion implant of claim 24 in which said body comprises a porous material.

36. The spinal fusion implant of claim 24 in which said body has an internal chamber and means for accessing said internal chamber.

37. The spinal fusion implant of claim 36 in which said internal chamber is capable of containing fusion promoting material.

38. The spinal fusion implant of claim 36 in which said body includes a wall surrounding said internal chamber.

39. The spinal fusion implant of claim 38 in which said wall has a plurality of openings passing therethrough in communication with said internal chamber.

40. The spinal fusion implant of claim 36 in which said body has means for closing said accessing means.

41. The spinal fusion implant of claim 24 in which one of said ends includes an engagement means for engaging instrumentation for the insertion of said implant.

42. The spinal fusion implant of claim 24 in which at least a portion of said outer surface comprises wells having at least partial walls.

43. The spinal fusion implant of claim 24 in which said implant is configured to be placed in close proximity in a side by side alignment to a second spinal fusion implant, said first and second implants when placed together having a combined overall width that is less than the sum of the individual maximum diameters of each of said first and second implants.

44. The spinal fusion implant of claim 24 in which said body has a longitudinal central axis and at least one truncated side forming a planar surface parallel to said central axis.

45. The spinal fusion implant of claim 44 in which said thread has a thread height measured from said body which is greatest at said truncated side.

46. An interbody spinal fusion implant for insertion across a disc space between adjacent vertebral bodies of a human spine, said implant comprising a body having a substantially cylindrical configuration, a longitudinal central axis and at least one truncated side forming a planar surface parallel to said central axis, said body having an insertion end, a trailing end, and an outer surface including a thread for engaging said implant to the adjacent vertebral bodies of the spine, the locus of said thread forming a substantially cylindrical configuration.

47. The spinal fusion implant of claim 46 in which said implant comprises a bone ingrowth material.

48. The spinal fusion implant of claim 46 in which said implant comprises a fusion promoting material.

49. The spinal fusion implant of claim 46 in which said implant is at least in part bioabsorbable.

50. The spinal fusion implant of claim 46 having a plurality of openings capable retaining fusion promoting material.

51. The spinal fusion implant of claim 46 in which said thread has a thread radius measured from the longitudinal central axis of said implant, said thread radius being substantially uniform for at least a portion of said implant.

52. The spinal fusion implant of claim 46 in which said thread has a thread radius measured from the longitudinal central axis of said implant, said thread radius being variable along at least a portion of said implant.

53. The spinal fusion implant of claim 46 in which said thread has a thread height measured from said body which is variable along at least a portion of said implant.

54. The spinal fusion implant of claim 46 in which said thread has a thread height measured from said body which is substantially constant along the length of said implant.

55. The spinal fusion implant of claim 46 body comprises a porous material.

56. The spinal fusion implant of claim 46 in which said body has an internal chamber and means for accessing said internal chamber.

57. The spinal fusion implant of claim 56 in which said internal chamber is capable of containing fusion promoting material.

58. The spinal fusion implant of claim 56 in which said includes a wall surrounding said internal chamber.

59. The spinal fusion implant of claim 56 in which said wall has a plurality of openings passing therethrough in communication with said internal chamber.

60. The spinal fusion implant of claim 56 in which said implant has means for closing said accessing means.

61. The spinal fusion implant of claim 46 in which one of said ends includes an engagement means for engaging instrumentation for the insertion of said implant.

62. The spinal fusion implant of claim 46 in which at least a portion of said outer surface comprises wells having at least partial walls.

63. The spinal fusion implant of claim 46 in which said implant is configured to be placed in close proximity in a side by side alignment to a second spinal fusion implant, said first and second implants when placed together having a combined overall width that is less than the sum of the individual maximum diameters of each of said first and second implants.

64. The spinal fusion implant of claim 46 in which said body has a second truncated side forming a planar surface parallel to said central axis and opposite to said one truncated side.

65. The spinal fusion implant of claim 64 in which said thread has a thread height measured from said body which is greatest at at least one of said truncated sides.

66. An interbody spinal fusion implant for insertion across a disc space between two adjacent vertebral bodies, said implant comprising a body having a substantially frusto-conical configuration along a sufficient portion of said body that is adapted to contact the adjacent vertebral bodies when implanted in the spine so as to maintain an angulation of the adjacent vertebral bodies relative to one another, said body having, an insertion end, a trailing end, and an outer surface including a thread for engaging said implant to the adjacent vertebral bodies of the spine, said implant being made of a material appropriate for human implantation.

67. The implant of claim 66 in which the outer locus of said thread forms a substantially cylindrical configuration.

68. The spinal fusion implant of claim 66 in which said insertion end is larger than said trailing end.

69. The spinal fusion implant of claim 68 in which said insertion end comprises a tapered leading portion.

70. The spinal fusion implant of claim 66 in which said trailing end is larger than said insertion end.

71. The spinal fusion implant of claim 66 in which said implant comprises a bone ingrowth material.

72. The spinal fusion implant of claim 66 in which said implant comprises a fusion promoting material.

73. The spinal fusion implant of claim 66 in which said implant is at least in part bioabsorbable.

74. The spinal fusion implant of claim 66 in which said body has a plurality of openings for retaining fusion promoting material.

75. The spinal fusion implant of claim 66 in which said thread has a thread radius measured from the longitudinal central axis of said implant, said thread radius being substantially uniform throughout the length of said implant.

76. The spinal fusion implant of claim 66 in which said thread has a thread radius measured from the longitudinal central axis of said implant, said thread radius being variable along the length of said implant.

77. The spinal fusion implant of claim 66 in which said thread has a thread height measured from said body which is variable along the length of said implant.

78. The spinal fusion implant of claim 66 in which said thread has a thread height measured from said body which is substantially constant along the length of said implant.

79. The spinal fusion implant of claim 66 in which said body comprises a porous material.

80. The spinal fusion implant of claim 66 in which said body has an internal chamber and an access opening for accessing said internal chamber.

81. The spinal fusion implant of claim 80 in which said internal chamber is capable of retaining fusion promoting material.

82. The spinal fusion implant of claim 80 in which said body includes a wall surrounding said internal chamber.

83. The spinal fusion implant of claim 82 in which said wall has a plurality of openings passing therethrough in communication with said internal chamber.

84. The spinal fusion implant of claim 80 in which said body has means for closing said accessing means.

85. The spinal fusion implant of claim 66 in which one of said ends includes an engagement means for engaging instrumentation for the insertion of said implant.

86. The spinal fusion implant of claim 66 in which at least a portion of said outer surface comprises wells having at least partial walls.

87. The spinal fusion implant of claim 66 in which said implant is configured to be placed in close proximity in a side by side alignment to a second spinal fusion implant, said first and second implants when placed together having a combined overall width that is less than the sum of the individual maximum diameters of each of said first and second implants.

88. The spinal fusion implant of claim 66 in which said body has a longitudinal central axis and at least one truncated side forming a planar surface parallel to said central axis.

89. The spinal fusion implant of claim 88 in which said thread has a thread height which when measured from said body is at its greatest on said truncated side.

90. The spinal fusion implant of claim 46 in which said thread has a thread height measured from said body which is greatest at said truncated side.

91. The spinal fusion implant of claim 24 in which said implant has an upper and lower portion for engaging the bone of the adjacent vertebral bodies, said upper and lower portions comprising a plurality of macroscopic openings.

92. The spinal fusion implant of claim 46 in which said implant has an upper and lower portion for engaging the bone of the adjacent vertebral bodies, said upper and lower portions comprising a plurality of macroscopic openings.

93. The spinal fusion implant of claim 66 in which said implant has an upper and lower portion for engaging the bone of the adjacent vertebral bodies, said upper and lower portions comprising a plurality of macroscopic openings.

94. The spinal fusion implant of claim 22 in which said thread is continuous over at least a portion of said truncated side.

95. The spinal fusion implant of claim 1 in which said thread has a height measured from said body that is larger at said trailing end than at said insertion end.

96. The spinal fusion implant of claim 1 in which said body has a plurality of openings passing therethrough so as to allow bone to grow from adjacent vertebral body to adjacent vertebral body and through said implant.

97. The spinal fusion implant of claim 22 in which said body has a second truncated side forming a planar surface parallel to said central axis and opposite to said one truncated side.

98. The spinal fusion implant of claim 24 in which said thread has a height measured from said body that is larger at said trailing end than at said insertion end.

99. The spinal fusion implant of claim 24 in which said body has a plurality of openings passing therethrough so as to allow bone to grow from adjacent vertebral body to adjacent vertebral body and through said implant.

100. The spinal fusion implant of claim 44 in which said body has a second truncated side forming a planar surface parallel to said central axis and opposite to said one truncated side.

101. The spinal fusion implant of claim 46 in which said body has a plurality of openings passing therethrough so as to allow bone to grow from adjacent vertebral body to adjacent vertebral body and through said implant.

102. The spinal fusion implant of claim 66 in which said thread has a height measured from said body that is larger at said trailing end than at said insertion end.

103. The spinal fusion implant of claim 66 in which said body has a plurality of openings passing therethrough so as to allow bone to grow from adjacent vertebral body to adjacent vertebral body and through said implant.

104. The spinal fusion implant of claim 88 in which said body has a second truncated side forming a planar surface parallel to said central axis and opposite to said one truncated side.

105. An interbody spinal fusion implant for insertion across a disc space between adjacent vertebral bodies of a human spine, said implant comprising:

a body having an outer surface, an insertion end, a trailing end, and a length between said insertion end and said trailing end, said body having transversely opposed arcuate portions oriented toward the adjacent vertebral bodies, said arcuate portions being in a diverging relationship to one another along a sufficient portion of the length of said body adapted to contact the adjacent vertebral bodies sufficient to maintain angulation of the vertebral bodies relative to one another, said outer surface comprising a thread for engaging said implant to the adjacent vertebral bodies of the spine.

106. The spinal fusion implant of claim 105 in which said trailing end is larger than said insertion end.

107. The spinal fusion implant of claim 105 in which said insertion end is larger than said trailing end.

108. The spinal fusion implant of claim 105 in which said body has a plurality of openings for retaining fusion promoting material.

109. The spinal fusion implant of claim 105 in which said thread has a thread radius measured from the longitudinal central axis of said implant, said thread radius being substantially uniform throughout at least a portion of said implant.

110. The spinal fusion implant of claim 105 in which said thread has a thread radius measured from the longitudinal central axis of said implant, said thread radius being variable along the length of said implant.

111. The spinal fusion implant of claim 105 in which said thread has a thread height measured from said body which is variable along the length of said implant.

112. The spinal fusion implant of claim 105 in which said body has an internal chamber and means for accessing said internal chamber.

113. The spinal fusion implant of claim 112 in which said body has means for closing said accessing means.

114. The spinal fusion implant of claim 105 in which at least a portion of said outer surface comprises wells having at least partial walls.

115. The spinal fusion implant of claim 105 in which said implant is configured to be placed in close proximity in a side by side alignment to a second spinal fusion implant, said first and second implants when placed together having a combined overall width that is less than the sum of the individual maximum diameters of each of said first and second implants.

116. The spinal fusion implant of claim 105 in which said body has a longitudinal central axis and at least one truncated side forming a planar surface parallel to said central axis.

117. The spinal fusion implant of claim 105 in which said arcuate portions are along the entire length of said body.

118. The spinal fusion implant of claim 105 in which the outer locus of the thread forms a substantially cylindrical configuration.

119. The spinal fusion implant of claim 105 in which the outer locus of the thread forms a substantially frusto-conical configuration.

120. The spinal fusion implant of claim 105 in which said implant is made of a material that is stronger than bone.

121. The spinal fusion implant of claim 1 in which said implant is made of a material that is stronger than bone.

122. The spinal fusion implant of claim 24 in which said implant is made of a material that is stronger than bone.

123. The spinal fusion implant of claim 46 in which said implant is made of a material that is stronger than bone.

124. The spinal fusion implant of claim 66 in which said implant is made of a material that is stronger than bone.

125. The spinal fusion implant of claim 1 in which said body has a length in the range of 10-32 mm.

126. The spinal fusion implant of claim 24 in which said body has a length in the range of 10-32 mm.

127. The spinal fusion implant of claim 46 in which said body has a length in the range of 10-32 mm.

128. The spinal fusion implant of claim 66 in which said body has a length in the range of 10-32 mm.

129. The spinal fusion implant of claim 105 in which said length is in the range of 10-32 mm.

130. The spinal fusion implant of claim 1 having a diameter at said insertion end in the range of 8-22 mm.

131. The spinal fusion implant of claim 24 having a diameter at said insertion end in the range of 8-22 mm.

132. The spinal fusion implant of claim 46 having a diameter at said insertion end in the range of 8-22 mm.

133. The spinal fusion implant of claim 66 having a diameter at said insertion end in the range of 8-22 mm.

134. The spinal fusion implant of claim 105 having a diameter at said insertion end in the range of 8-22 mm.

135. The spinal fusion implant of claim 1 having a diameter at said trailing end in the range of 10-24 mm.

136. The spinal fusion implant of claim 24 having a diameter at said trailing end in the range of 10-24 mm.

137. The spinal fusion implant of claim 46 having a diameter at said trailing end in the range of 10-24 mm.

138. The spinal fusion implant of claim 66 having a diameter at said trailing end in the range of 10-24 mm.

139. The spinal fusion implant of claim 105 having a diameter at said trailing end in the range of 10-24 mm.

140. A fusion device for facilitating arthrodesis in the disc space between adjacent vertebrae, comprising:
an elongated body having a length, a first diameter at a first end and a larger second diameter at a second end opposite said first end, said first and second diameters sized to be greater than the space between the adjacent vertebrae;
said body having an outer surface that is substantially continuously tapered from said first end to said second end with external threads defined on said outer surface and extending substantially entirely along said length of said body.

141. The fusion device according to claim 140, wherein said body is formed of a porous biocompatible material to permit bone tissue ingrowth into the device.

142. The spinal fusion implant of claim 116 in which said body has a second truncated side forming a planar surface parallel to said central axis and opposite to said one truncated side.

143. The spinal fusion implant of claim 105 in which said body has a plurality of openings passing therethrough so as to allow bone to grow from adjacent vertebral body to adjacent vertebral body and through said implant.

144. The spinal fusion implant of claim 1 in which said thread has a thread radius measured from the longitudinal central axis of said implant, said thread radius being substantially uniform throughout at least a portion of said implant.

145. The spinal fusion implant of claim 24 in which said body has a substantially frusto-conical configuration.

146. The spinal fusion implant of claim 24 in which said body has at least in part a cylindrical configuration.

147. The spinal fusion implant of claim 1, further in combination with a fusion promoting substance.

148. The spinal fusion implant of claim 147, wherein said fusion promoting substance is bone morphogenetic protein.

149. The spinal fusion implant of claim 147, wherein said fusion promoting substance includes hydroxyapatite.

150. The spinal fusion implant of claim 147, wherein said fusion promoting substance includes hydroxyapatite tricalcium phosphate.

151. The spinal fusion implant of claim 147, wherein said fusion promoting substance is bone.

152. The spinal fusion implant of claim 24, further in combination with a fusion promoting substance.

153. The spinal fusion implant of claim 152, wherein said fusion promoting substance is bone morphogenetic protein.

154. The spinal fusion implant of claim 152, wherein said fusion promoting substance includes hydroxyapatite.

155. The spinal fusion implant of claim 152, wherein said fusion promoting substance includes hydroxyapatite tricalcium phosphate.

156. The spinal fusion implant of claim 152, wherein said fusion promoting substance is bone.

157. The spinal fusion implant of claim 46, further in combination with a fusion promoting substance.

158. The spinal fusion implant of claim 157, wherein said fusion promoting substance is bone morphogenetic protein.

159. The spinal fusion implant of claim 157, wherein said fusion promoting substance includes hydroxyapatite.

160. The spinal fusion implant of claim 157, wherein said fusion promoting substance includes hydroxyapatite tricalcium phosphate.

161. The spinal fusion implant of claim 157, wherein said fusion promoting substance is bone.

162. The spinal fusion implant of claim 66, further in combination with a fusion promoting substance.

163. The spinal fusion implant of claim 162, wherein said fusion promoting substances is bone morphogenetic protein.

164. The spinal fusion implant of claim 162, wherein said fusion promoting substance includes hydroxyapatite.

165. The spinal fusion implant of claim 162, wherein said fusion promoting substance includes hydroxyapatite tricalcium phosphate.

166. The spinal fusion implant of claim 162, wherein said fusion promoting substance is bone.

167. The spinal fusion implant of claim 105, further in combination with a fusion promoting substance.

168. The spinal fusion implant of claim 167, wherein said fusion promoting substance is bone morphogenetic protein.

169. The spinal fusion implant of claim 167, wherein said fusion promoting substance includes hydroxyapatite.

170. The spinal fusion implant of claim 167, wherein said fusion promoting substance includes hydroxyapatite tricalcium phosphate.

171. The spinal fusion implant of claim 167, wherein said fusion promoting substance is bone.

172. A fusion device for facilitating arthrodesis in the disc space between adjacent vertebrae, comprising:
an elongated body having a length and an outer surface extending along said length, said outer surface including a pair of oppositely disposed arcuate portions and a pair of substantially flat portions extending between said pair of arcuate portions, said pair of arcuate portions defining external threads extending substantially entirely along said length of said body, said pair of substantially flat portions extending along a substantial portion of said length of said body, said pair of substantially flat portions terminating adjacent a first end of said elongated body, said external threads defining at least one circumferentially continuous thread extending along a majority of the length of said elongated body.

173. The fusion device according to claim 172, wherein said pair of opposite arcuate portions defines an outer dimension adjacent a first end of said elongated body, said outer dimension being adapted for engagement within a lesser dimension of the disc space.

174. The fusion device according to claim 172, wherein said elongated body defines a hollow interior.

175. A fusion device for facilitating arthrodesis in the disc space between adjacent vertebrae, comprising:
an elongated body having a length and an outer surface extending along said length, said outer surface including a pair of oppositely disposed arcuate portions and a pair of substantially flat portions extending between said pair of arcuate portions, said pair of arcuate portions defining an external thread extending substantially entirely along said length of said body, said pair of substantially flat portions extending along a substantial portion of said length of said body, said substantially flat portions being interrupted by said thread, said elongated body defining a hollow interior, said pair of arcuate portions each defining at least one opening extending therethrough in communication with said hollow interior.

176. The fusion device according to claim 175, further comprising a bone growth inducing material disposed within said hollow interior.

177. The fusion device according to claim 175, wherein said pair of substantially flat portions are disposed generally opposite one another.

178. The fusion device according to claim 175, wherein said pair of substantially flat portions are substantially parallel to one another.

179. The fusion device according to claim 175, wherein said openings defined by said pair of arcuate portions are disposed generally opposite one another.

180. The fusion device according to claim 175, wherein said pair of arcuate portions are tapered along a substantial portion of said length of said elongated body.

181. The fusion device according to claim 175, further comprising an insertion instrument adapted to implant the fusion device within the disc space between the adjacent vertebrae.

182. An interbody spinal fusion implant for insertion within an implantation space formed across the height of a disc space between adjacent vertebral bodies of a human spine, said implant comprising:
a body having a leading end for insertion first into the disc space, a trailing end opposite said leading end, a central longitudinal axis therebetween, and a length along the central longitudinal axis, said body having opposed arcuate portions between said leading and trailing ends adapted to be placed within the implantation space oriented toward the adjacent vertebral bodies, respectively, said opposed arcuate portions having at least one opening therethrough, said openings being in communication with one another to permit for the growth of bone from adjacent vertebral body to adjacent vertebral body through said implant, said body having at least one truncated side along at least a portion of the central longitudinal axis between said opposed arcuate portions and between said leading and trailing ends; and
a thread along at least a portion of the length of said body adapted to engage said implant to the adjacent vertebral bodies, said thread having a thread height measured from said body which is greatest at said at least one truncated side, said at least one truncated side having a truncated portion between said thread and said leading end.

183. An interbody spinal fusion implant for insertion within an implantation space formed across the height of a disc space between adjacent vertebral bodies of a human spine, said implant comprising:
a body having a leading end for insertion first into the disc space, a trailing end opposite said leading end, a mid-longitudinal axis through said leading and trailing ends, and opposed arcuate portions between said leading and trailing ends adapted to be placed within the implantation space oriented toward the adjacent vertebral bodies, respectively, said opposed arcuate portions having at least one opening therethrough, said openings being in communication with one another to permit for the growth of bone from adjacent vertebral body to adjacent vertebral body through said implant; and
a thread adapted to engage said implant to the adjacent vertebral bodies, said thread having a thread height measured from said body, said thread height being variable along more than one turn of said thread about the mid-longitudinal axis of said body.

* * * * *

UNITED STATES PATENT AND TRADEMARK OFFICE
CERTIFICATE OF CORRECTION

PATENT NO. : 7,534,254 B1
APPLICATION NO. : 08/480908
DATED : May 19, 2009
INVENTOR(S) : Gary Karlin Michelson It is certified that error appears in the above-identified patent and that said Letters Patent is hereby corrected as shown below:

<u>Cover Page 1, Section (56) References Cited, U.S. Patent Documents</u>:
Column 1, line 2: change "1,137,858" to -- 1,137,585 --; and
Column 2, line 2: change "Moreira" to -- De G. Moreira --.

<u>Cover Page 2, Section (56) References Cited, U.S. Patent Documents</u>:
Column 1, line 18: change "3,720,595" to -- 3,720,959 --.

<u>Cover Page 3, Section (56) References Cited, Foreign Patent Documents</u>:
Column 1, line 2: delete "DE   26 46 039   4/1975".

<u>Cover Page 4, Section (56) References Cited, Other Publications</u>:
Column 1, line 9: change "Compnay" to -- Company --;
Column 1, line 22: change "Orthapaedics" to -- Orthopaedics --;
Column 1, line 55: change "Debowes" to -- DeBowes --;
Column 1, line 56: change "Reseach" to -- Research --; and
Column 2, line 6: change "Conventry" to -- Coventry --.

<u>Column 9, Line 46</u>:
Change "and a means" to -- and means --.

<u>Column 16, Line 39</u>:
Change "substances" to -- substance --.

Signed and Sealed this

Twenty-second Day of December, 2009

David J. Kappos
*Director of the United States Patent and Trademark Office*